(12) United States Patent
Feng et al.

(10) Patent No.: US 8,598,225 B2
(45) Date of Patent: Dec. 3, 2013

(54) USE OF L-BUTYLPHTHALIDE IN THE MANUFACTURE OF MEDICAMENTS FOR TREATMENT OF CEREBRAL INFARCT

(75) Inventors: Yipu Feng, Beijing (CN); Xiaoliang Wang, Beijing (CN); Jinghua Yang, Beijing (CN); Ying Peng, Beijing (CN)

(73) Assignee: CSPC Zhongqi Pharmaceutical Technology (Shijiazhuang) Co., Ltd., Shijiazhuang (CN)

( * ) Notice: Subject to any disclaimer, the term of this patent is extended or adjusted under 35 U.S.C. 154(b) by 0 days.

(21) Appl. No.: 12/908,520

(22) Filed: Oct. 20, 2010

(65) Prior Publication Data

US 2011/0082201 A1    Apr. 7, 2011

Related U.S. Application Data

(63) Continuation of application No. 10/574,917, filed as application No. PCT/CN2004/001123 on Sep. 29, 2004, now abandoned.

(30) Foreign Application Priority Data

Oct. 10, 2003    (CN) .......................... 2003 1 0100222

(51) Int. Cl.
    A61K 31/34      (2006.01)
    A61K 31/335     (2006.01)
    A61K 31/36      (2006.01)
(52) U.S. Cl.
    USPC ............ 514/461; 514/462; 514/465; 514/466
(58) Field of Classification Search
    USPC .................................. 514/461, 462, 465, 466
    See application file for complete search history.

(56) References Cited

U.S. PATENT DOCUMENTS

| | | | |
|---|---|---|---|
| 5,733,524 | A | 3/1998 | Bucala et al. |
| 5,744,500 | A | 4/1998 | Youdim et al. |
| 5,914,112 | A | 6/1999 | Bednar et al. |
| 6,106,830 | A | 8/2000 | Li |
| 6,350,739 | B1 | 2/2002 | Simpkins et al. |
| 6,399,576 | B1 | 6/2002 | Li |
| 6,447,814 | B1 | 9/2002 | Lee et al. |
| 6,689,808 | B2 | 2/2004 | Guo et al. |
| 6,716,822 | B2 | 4/2004 | Lee et al. |
| 6,852,687 | B2 | 2/2005 | Tsubota et al. |
| 6,930,096 | B2 | 8/2005 | Foguet et al. |
| 7,129,272 | B2 | 10/2006 | Ueno et al. |
| 7,256,198 | B2 | 8/2007 | Dollings et al. |
| 7,482,027 | B2 | 1/2009 | Kim et al. |
| 2002/0025985 | A1 | 2/2002 | Ueno et al. |
| 2003/0219430 | A1 | 11/2003 | Faerman et al. |
| 2005/0233004 | A1 | 10/2005 | Shin et al. |
| 2006/0166931 | A1 | 7/2006 | Niu et al. |
| 2006/0246157 | A1 | 11/2006 | Kim et al. |
| 2007/0042057 | A1 | 2/2007 | Raederstorff et al. |
| 2007/0082947 | A1 | 4/2007 | D'Orazio et al. |
| 2007/0112065 | A1 | 5/2007 | Feng et al. |

FOREIGN PATENT DOCUMENTS

| | | |
|---|---|---|
| CN | 1 100 097 A | 3/1995 |
| CN | 1 257 706 A | 6/2000 |
| CN | 1 375 288 A | 10/2002 |
| JP | 63-083080 | 4/1988 |
| RU | 2 139 851 C1 | 10/1999 |

OTHER PUBLICATIONS

Q. Chang, et al., "Effects of chiral 3-n-butylphthalide on apoptosis induced by transient focal cerebral ischemia in rats," Acta Pharmacologica Sinica 24(8): 796-804 (2003).
H. Xu, et al., "Effects of 3-n-butylphthalide on pial arteroles infocal cerebral ishcheia rats," Acta Pharmaceutica Sinica 34(3): 172-175 (1999).
H. Xu, et al., "Inhibitory effects of chiral 3-n-butylphthalide on inflammation following focal ischemic brain injury in rats," Database Accession No. PREV200000331032, abstract only, (2000).
Abstract of CN 20042018722, Database EPODOC, European Patent Office, The Hague, NL.
Z. Chong, et al., "Effect of dl-3-n-butylphthalide on the activity of the choline acetyltransferase in ischemic brain and cultured neurons subjected to hypoglycemia/hypoxia," Chinese Pharmaceutical Journal 34(8): 519-522 (1999).
C. H. Yan, et al., "Effect of dl-3-n-butylphthalide on striatum cerebral blood flow in normal and middle cerebral artery occlusion rats," Chinese Journal of Pharmacology and Toxicology 12(1): 36-39 (1998).
J. F. Lin, et al., "Effect of dl-3-n-butylphthalide on delayed neuronal damage after focal cerebral ischemia and intrasynaptosomes calcium in rats," Database Accession No. PREV199699158021 (1996).
X. G. Liu, et al., "Protective effect of dl-3-n-butylphthalide on ischemic neurological damage and abnormal behavior in rats subjected to focal ischemia," Database Accession No. NLM8712015 (1995).
L. Y. Zhang, et al., "Effect of dl-3-n-butylphthalide (NBP) on life span and neurological deficit in SHRsp rats," Database Accession No. NLM8762459 (1996).
C. H. Yan, et al., "Effects of dl-3-n-butylphthalide on regional cerebral blood flow in right middle cerebral artery occlusion rats," Acta Pharmacological Sinica 19(2): 117-120 (1998).
Abstract of CN1 166 693, Database EPODOC, European Patent Office, The Hague, NL.
Supplementary European Search Report dated Jan. 14, 2010, issued in corresponding European Patent Application No. 04762256.8.
Guo, et al., Chin Med J 119(6): 662-668 (2006).
Shimamura, et al., Cir 109: 424-431 (2004).

(Continued)

*Primary Examiner* — Kevin E Weddington
(74) *Attorney, Agent, or Firm* — Kenyon & Kenyon LLP (57) ABSTRACT

The present invention discloses the use of L-butylphthalide of formula (I) in the manufacture of medicaments for the prevention and treatment of cerebral infarct, especially induced by focal cerebral ischemia.

(I)

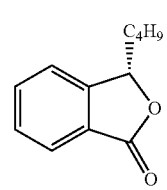

4 Claims, 3 Drawing Sheets

(56) References Cited

OTHER PUBLICATIONS

Izozumi, et al., Tokai J Exp Clin Med 23(3): 103-117 (1998).

J. Xiong, et al., "*The protective effect of butylphthalide against mitochondrial injury during cerebral ischemia*," Acta Pharmaceutica Sinica 35(6): 408-412 (2000).

Yepes, et al., Blood 96: 569-576 (2000).

Canadian Office Action, dated Mar. 3, 2009, issued in the corresponding Canadian Patent Application No. 2,549,931.

*The Merck Manual of Therapy and Diagnosis*, $17^{th}$ ed. Whitehouse Station, N.J.: Merck Research Laboratories, p. 1417-1424 (1999).

Russian Decision on Granting and the allowed claims, dated Mar. 17, 2008, issued in the corresponding Russian Patent Application No. 2006115784 (Russian Patent No. 2336870).

Y. Peng, et al., "*Antiplatelet and antithrombotic activity of L-3-n-butylphthalide in rats*," J. Cardiovasc., Pharmacol. 43(6): 876-881 (2004).

Xing-Wang, "3-n-Butylphthalide", Drugs of the Future 25(1): 16-23, 2000.

Oral Proceedings Notification, dated Jul. 19, 2013, issued in corresponding European Patent Application No. 04762256.8.

USE OF L-BUTYLPHTHALIDE IN THE MANUFACTURE OF MEDICAMENTS FOR TREATMENT OF CEREBRAL INFARCT

This is a continuation of U.S. patent application Ser. No. 10/574,917, filed Apr. 11, 2006 now abandoned, which is a national phase application of International Application No. PCT/CN2004/001123 filed Sep. 29, 2004, claiming priority to Chinese Application No. 2003-10100222.2 filed Oct. 10, 2003, the disclosure of U.S. patent application Ser. No. 10/574,917 is incorporated by reference.

FIELD OF THE INVENTION

The present invention relates to the use of L-n-butylphthalide and the composition comprising the same in the manufacture of medicaments for prevention and treatment of cerebral infarct, especially cerebral infarct induced by focal cerebral ischemia.

BACKGROUND OF THE INVENTION

Cerebrovascular diseases have become one of the major leading causes of death in China, and better therapeutic agents for treatment of acute ischemic cerebral stroke are needed all over the world. Thrombolytic agent, t-PA, which was approved by U.S. Food and Drug Administration (FDA) in 1996, has contentious therapeutic effect on these diseases due to its side effect related to high risk of encephalic bleeding. The results of studies on various cerebral protective agent has shown that the clinical therapeutic effects of many medicaments are either insufficient, or have relatively severe side effects. Several medicaments are still in the phase of clinical trial.

In recent more than 10 years, the present inventors have found that racemic butylphthalide (or butylphthalide, NBP) is a drug that has significant therapeutic effect on acute ischemic cerebral stroke. The pharmacodynamical characteristics thereof include: 1. improving energy metabolism of the ischemic brain; 2. significantly reducing the area of cerebral infarct induced by focal cerebral ischemia in rat, and alleviating deficit of neural function; 3. alleviating the cerebral edema induced by focal cerebral ischemia; 4. significantly improving the focal cerebral blood flow in ischemic area and micro-circulation in cerebral pia mater of rats; and 5. significantly alleviating the memory disorder induced by focal cerebral ischemia.

Moreover, it has less toxic side effect. The present applicant has obtained two use patents on the related field in China, which is China Patent No. ZL93117148 titled "Use of butylphthalide in the manufacture of medicaments for prevention and treatment of diseases induced by cerebral ischemia" issued in 1999, and Chinese Patent No. ZL98125618.X titled "Use of butylphthalide in the manufacture of anti-thrombosis medicaments" issued in 2002 under the International Patent Classification No. A61K31/34, respectively.

After the pre-clinical studies, clinical trials of phase II and phase III were conducted on 542 cases, in which there are 192 cases using multi centered, random, double blinded placebo control. It was found that the total effective rate in the administration group is 70.7%, and the rate in placebo group is 41.0%. Thus good therapeutic effect was obtained. The New Drug Certificate and Production License for the class I new drug have been approved on NBP for the treatment of acute ischemic cerebral stroke by the State Drug Administration of China in 2002 (National Drug License Nos. H20020374; H20020375; 2002H0551, and 2002H0552).

Chemical resolution was conducted on racemic butylphthalide (simplified as dl-NBP hereinafter), and levobutylphthalide (simplified as l-NBP hereinafter) and dextrobutylphthalide (simplified as d-NBP hereinafter) are obtained separately. The present applicant has filed a China Patent Application No. 99109673.8 with a Publication No. CN1283621A, the title of which is "A method for preparing the optical active 3-n-butylphthalide". Furthermore, the function of L-butylphthalide was not mentioned in the previous China Patent No. ZL93117148.

SUMMARY OF THE INVENTION

In order to overcome the disadvantages of the prior art, the present invention provides the use of L-n-butylphthalide (simplified as l-NBP hereinafter) of formula (I)

in the manufacture of the medicaments for prevention or treatment of cerebral infarct.

L-n-butylphthalide used in the present invention is obtained by firstly chemically synthesizing racemic n-butylphthalide, and then chemically resolving to produce a levorotary optical isomer of n-butylphthalide. After analyzing by nuclear magnetic spectroscopic analysis, mass spectrum analysis, infrared spectral analysis and the like, especially by using chiral gas chromatography column (Chiraldex G-TA) in HP 5890 gas chromatograph, it was confirmed that the product is a single optical stereoisomer, ie. levorotary n-butylphthalide, in terms of optical purity and chemical purity (specific optical activity $>-66.49°$, optical purity >98%, and chemical purity >98%). Method of resolution was disclosed in China Patent Application titled "A method for preparing the optical active 3-n-butylphthalide" with an Application No. 99109673.8 and a Publication No. CN1283621. The product has an identical chemical formula to that of n-butylphthalide contained in celery and seeds thereof.

The present studies have shown that the optical isomer, l-NBP, has better therapeutic effect on cerebral ischemia of rats than d-NBP and better than dl-NBP containing the same amount of l-NBP.

Figure 1:
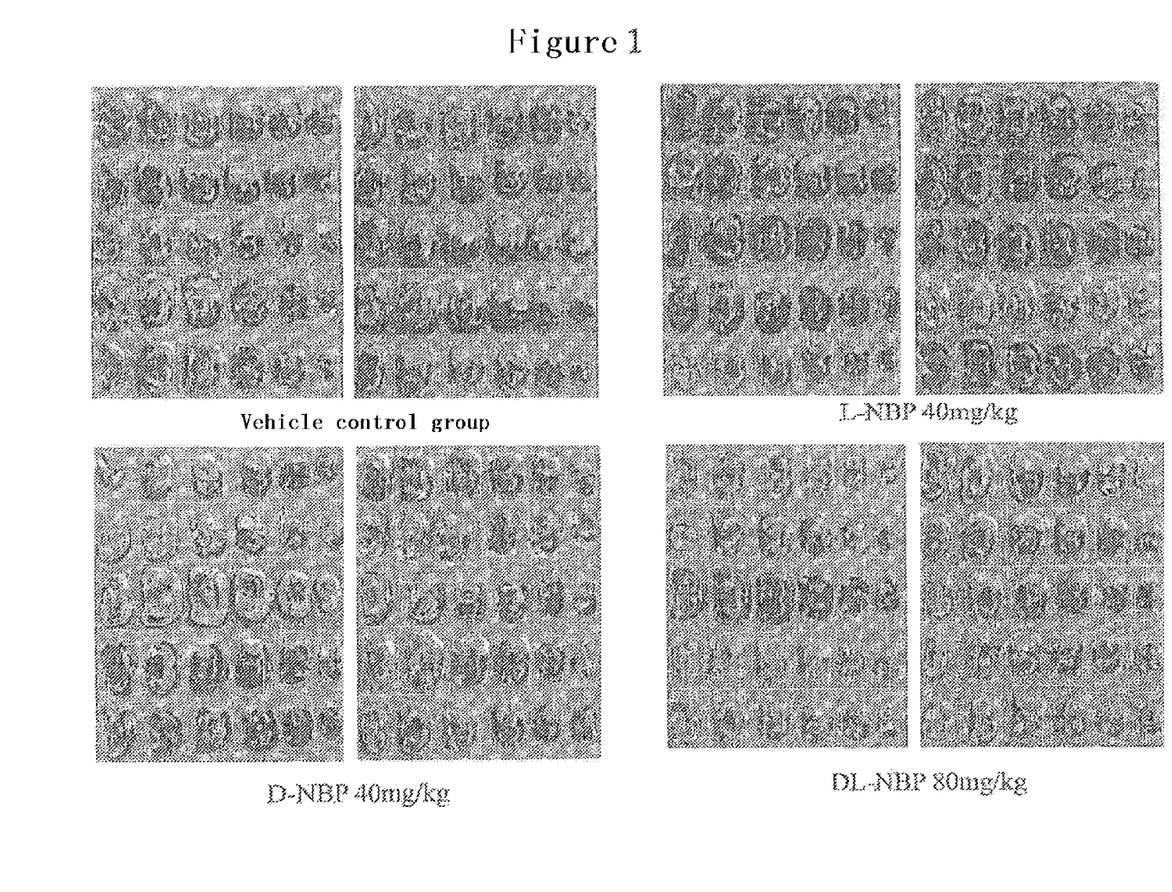
FIG. 1 is the digital photograph showing the effects on the cerebral infarct volume of rats of administering NBP by gavage 15 minutes after transient middle cerebral artery occlusion.
Figure 2:
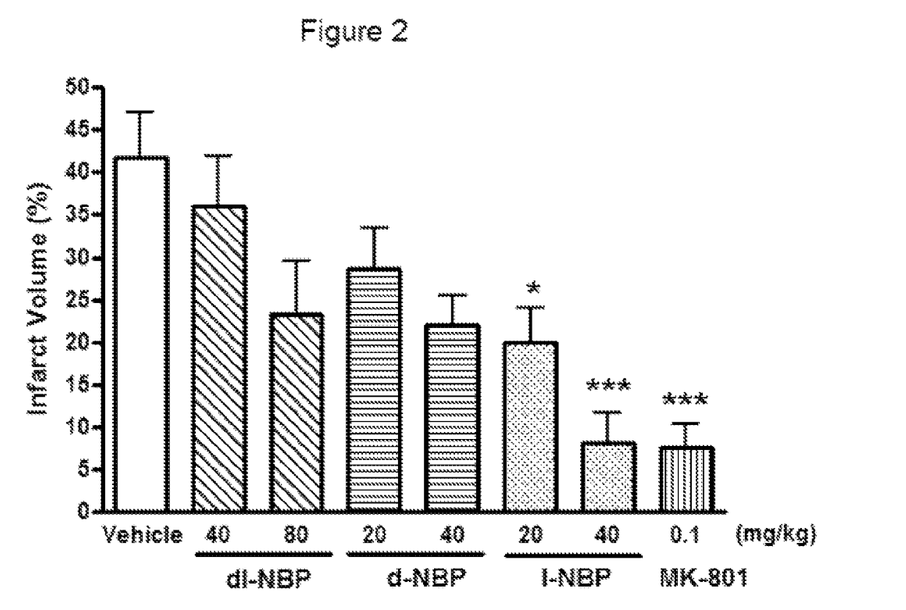
FIG. 2 shows the effects on the cerebral infarct volume of rats of administering NBP by gavage 15 minutes after transient middle cerebral artery occlusion. The data are expressed as the volume percentage obtained by dividing infarct portion by that of the contralateral (normal) hemisphere, and expressed as mean±standard error.
*$P<0.05$, $P<0.01$, *$P<0.001$, vs. vehicle group.

In the studies, the therapeutic effect of optical active NBP on cerebral ischemia was observed by using the rat model of ischemic cerebral stroke, which was prepared by 2 hours of middle cerebral artery occlusion and then 24 hours of reperfusion. Transient focal cerebral ischemic rats were divided into 8 groups with 10 rats in each group. Group 1) was vehicle control with 1 ml/kg of vegetable oil; groups 2) and 3) were 40 and 80 mg/kg of dl-NBP; groups 4) and 5) were 20 and 40 mg/kg of d-NBP; groups 6) and 7) were 20 and 40 mg/kg of l-NBP; and group 8 was 0.1 mg/kg of MK801. Animals in groups 1-7 were orally administered, and animals in group 8 were intraperitoneally administered. Solvent of butylphthalide and positive drug for control were administered 15 minutes after transient focal cerebral ischemia was induced in rats. The presence of significant difference between each group analyzed by one-way ANOVA indicated that the infarct volume was significantly reduced dose-dependently in l-NBP group (both in 20 mg/kg and 40 mg/kg). The reducing effect in the group of 40 mg/kg was the highest, and the infarct volume was reduced up to 80.4% (p<0.001, vs. vehicle group). The therapeutic effect in this group is similar to that of MK801 group (infarct volume was reduced to 81.8%, p<0.001), while no significant effect was observed in d-NBP and dl-NBP groups (see FIGS. 1 and 2). The above results showed that the reducing effect of l-NBP on the infarct volume is higher than that of d-NBP. Although the infarct volumes in dl-NBP (80 mg/kg) and d-NBP (40 mg/kg) groups were reduced as compared with vehicle control, there was no statistically difference between them. Since dl-NBP (80 mg/kg) comprises l-NBP (40 mg/mg), the result suggested that the presence of d-NBP in dl-NBP possibly antagonises the effect of l-NBP.

By behavioral evaluation, the neurological score of most animals in vehicle control group were 2, manifested as contralateral forelimbs flexion and decreased resistance to lateral push. Contralateral circling occurred in fewer rats, and they were graded with a score of 3. Even fewer animals only manifested as contralateral forelimb flexion and were graded with 1; or had severe symptoms and absence of autonomous movement, which was graded with 4. The mean of neurological scores of animals in vehicle control group was 2.6±0.3. Oral administration of 20 or 40 mg/kg of l-NBP 15 minutes after ischemia was shown to improve the neurological symptoms (1.4, p<0.01; and 1.1, p<0.001), and the potency of MK801 was the most significant (0.8, p<0.001), while no significant improvement was observed in groups of d-NBP and dl-NBP. As for animals in MK801 treatment group, although the symptoms induced by cerebral ischemia was significantly reduced, the limbs were weak, and staggered when sprawling, ataxia occurred, and unilaterally circled. The behavioral evaluation suggests that the improvement extent on behavior is in parallel with the reducing effect of the drug on the infarct volume.

In summary, the present invention was performed on the levels of biochemistry, molecular biology and on animal level, and consistent results were obtained, that is, the cerebral protective effect of l-NBP is higher than those of d-NBP and dl-NBP, and the presence of d-NBP in dl-NBP antagonises the action of l-NBP, so that the protective effect against cerebral ischemia of dl-NBP is reduced.

Previous studies have shown that the effects of l-NBP against platelet aggregation and against thrombosis are similar to those of Aspirin and Ticlipidine. In addition, l-NBP also has cerebral protective effect and micro-circulation improving effect (d-NBP has no such effect), which are not possessed by Aspirin and Ticlipidine. Therefore, l-NBP has so wide a therapeutic spectrum, that it can be used for the treatment of acute ischemic cerebral stroke, as well as secondary prevention of the cerebral stroke, prevention of cardiac infarct, and treatment of peripheral vascular diseases.

The present invention follows the development of international new drug discovery to increase therapeutic effect and reduce toxic side effect by resolving the racemic drug into optical monomers, making the characteristics of each clear, and developing the optical isomers with potent effect or low toxic side effect into chiral new drugs. In the context, l-NBP in racemic butylphthalide has relatively potent inhibitory effect against cerebral ischemia. d-NBP not only has weak effect, but also antagonise the inhibitory effect of l-NBP against cerebral ischemia. Therefore, it is reasonable to develop L-butylphthalide into a new chiral drug for the treatment of acute ischemic cerebral stroke.

The present invention also relates to the pharmaceutical composition comprising the compound of the present invention as active ingredient, and conventional pharmaceutically acceptable vehicles or adjuvant. Generally, the pharmaceutical composition of the present invention comprises 0.1-95% by weight of the compound of the present invention.

The pharmaceutical composition comprising the compound of the present invention may be prepared according to the method well known in the art. For this purpose, the compound of the present invention may be combined with one or more solid or liquid pharmaceutically acceptable vehicles and/or adjuvant if desired, so as to be formulated into suitable administration forms or dosage forms for human use or veterinary use.

The compound of the present invention and the composition comprising the same may be administered in unit dosage form, and the administration route may be intestinal or parenteral, such as oral, intramuscular, subcutaneous, nasal, oral mucousal, transdermal, intraperitoneal, rectal administration, or the like.

The administration route of the compound of the present invention or the pharmaceutical composition comprising the same may be injection, including intravenous injection, intramuscular injection, subcutaneous injection, intracutaneous injection, and acupoint injection.

The administration formulation may be liquid formulation or solid formulation. For example, the liquid formulation may be solution, colloid, microparticulate, emulsion, and suspension. Other formulations may also be used, such as tablet, capsule, pill, aerosol, pellet, powder, solution, suspension, emulsion, particulate, suppository, and lyophilized powder, and the like.

The compound of the present invention may be prepared to be conventional formulations, as well as sustained release formulations, control released formulations, targeting formulations, and various micro-particular administration systems.

Various vectors well known in the art may be widely used so as to prepare the unit dosage form into tablets. Examples of vectors are, for example, diluents and absorbants, such as starch, dextrin, calcium sulfate, lactose, mannitol, sucrose, sodium chloride, glucose, urea, calcium carbonate, bolus alba, microcrystalline cellulose, aluminum silicate, and the like; wetting agents and bonding agents, such as water, glycerol, polyethylene glycol, ethanol, propanol, starch slurry, dextrin, syrup, honey, glucose solution, gum arabic slurry, gelatin slurry, sodium carboxymethyl cellulose, shellac, methyl cellulose, potassium phosphate, polyvinylpyrrolidone, and the like; disintegrant, such as dry starch, alginate, agar powder, Phaeophyta starch, sodium bicarbonate and citric acid, calcium carbonate, polyoxyethylene sorbitan fatty acid ester, sodium lauryl sulfonate, methyl cellulose, ethyl cellulose, and the like; disintegration inhibiting agents, such as sucrose, glycerol tristearate, cacao butter, hydrogenated oil, and the like; absorption promoting agent, such as quarternary ammonium salt, sodium dodecyl sulfate, and the like; lubricant, such as talc powder, silica dioxide, corn starch, stearate salt, boric acid, liquid paraffin, polyethylene glycol, and the like. The tablets may be further formulated as coated tablets, such as sugar-coated tablets, film-coated tablets, enteric coated tablets, or bilayer tablets and multilayer tablets.

In order to formulate the unit dosage form into pellets, for example, various vectors well known in the art may be widely used. Examples of vectors are, for example, diluents and absorbants, such as glucose, lactose, starch, cacao butter, hydrogenated vegetable oil, polyvinylpyrrolidone, kaoline, talc powder, and the like; bonding agents, such as gum arabic, tragacanth gum, gelatin, ethanol, honey, liquid sugar, rice paste or panada; disintegrants, such as agar powder, dry starch, alginate, sodium lauryl sulfonate, methyl cellulose, ethyl cellulose, and the like.

In order to formulate the unit dosage form into capsules, the compound of the present invention as active ingredients is mixed with various vectors described above, the thus obtained mixture is placed into the hard gelatin capsules or soft capsules. The compound of the present invention as active ingredients may also be formulated into microcapsules, mixed with aqueous medium to form into suspensions, and filled into hard capsules or formulated into injections for use.

For example, the compound of the present invention may be formulated into formulations for injection, such as solution, suspension, emulsion, lyophilized powder for injection, which may be aqueous or non-aqueous, may comprise one and/or more pharmaceutically acceptable vectors, diluent, bonding agent, lubricant, perservative, surfactant, or dispersant. Diluent may be selected, for example, from water, ethanol, polyethylene glycol, 1,3-propylene glycol, ethyoxylated isostearyl alchol, multi-oxylated isostearyl alchol, polyoxyethylene sorbitan fatty acid ester, and the like. Furthermore, suitable amount of sodium chloride, glucose or glycerol may be added into the formulations for injection in order to prepare isotonic injections. Conventional solving agent, buffering agents, pH adjusting agents may also be added. These adjuvants are commonly used in the art.

Moreover, coloring agents, perservatives, flavors, flavoring agents, sweetening agents, or the like may be added to the pharmaceutical formulations if desired.

In order to achieve the administration purpose and increase the therapeutic effect, the medicament or the pharmaceutical composition may be administered by any administration method well known in the art.

The administration dose of the pharmaceutical composition comprising the compound of the present invention depends on many factors, such the nature or severity of the disease to be prevented or treated, sex, age, body weight, trait and individual response of the patient or the animal, the administration route, the administration frequency and therapeutic purpose. Therefore, the therapeutic dose in the present invention may vary in a wide range. Generally, the dose of the pharmaceutical ingredients in the present invention is well known to those skilled in the art, and may be suitably adjusted depending on exact amount of the drug contained in the final formulation of the composition comprising the compound of the present invention, to reach a therapeutically effective dose, and thus accomplish the preventive or therapeutic purpose of the present invention. The suitable daily dose preferably lies in the range from 0.1 to 100 mg/kg body weight, more preferably from 0.1 to 100 mg/day/person. The dosage may be in unit dosage form or divided into more than one, for example 2, 3, or 4 dosage forms for administration, which depends on the clinical experience of the administers, and includes other dosage regimes using other therapeutic means.

Total dose needed in each therapy may be administered in more than one dosage, or administered in one dosage. The compound or the composition of the present invention may be administered alone, or used in combination with other therapeutic agents or heteropathic agents with adjusted dosage.

Terms
dl-NBP: racemic butylphthalide
d-NBP: dextral butylphthalide
l-NBP: levorotatory n-butylphthalide
tMCAO: transient focal cerebral ischemic model

DETAILED DESCRIPTION OF THE INVENTION

EXAMPLE 1

Effects of Optical Butylphthalide on the Cerebral Infarct Volume of tMCAO Rats

Experimental Materials And Methods
Reagents And Drugs
l-, d-, and dl-NBP were all provided by department of synthetic pharmaceutical chemistry of our institute, both optical and chemical purity of which are >99%, and the optical activity of which is −66.49°, +66.88° and 0°, respectively. They were formulated with vegetable oil. MK801 is the product of Sigma, and was formulated with physiological brine. Triphenyltetrazolium chloride (TTC), which was manufactured by Beijing Chemical Plant, was formulated with distilled water into 4% solution for use.

Preparation of Transient Focal Cerebral Ischemic Model (tMCAO)

Male Wistar rats weighed 280-320 g were used, with each 5 rats kept in one cage. Animals were allowed free access to food and water at room temperature controlled at 23° C. The rats were anesthetized with 40 mg/kg of sodium pentobarbital. Under the surgical microscope, a midline neck skin incision was make to expose the right common cartotid artery, and the internal carotid artery (ICA) and external carotid artery (ECA) were then separated free from surrounding nerves and fascia, and the anastomotic branch was ligated. The ECA were ligated and cut, pulled to be straight and in line with ICA. A nylon suture with rounded tip and the diameter of 0.28 mm (coated with poly-L-lysine) was introduced from ECA into the lumen of the ICA for about 20 mm, advancing endocranially to the starting point of middle cerebral artery.

After 2 h of ischemia, the nylon suture was carefully withdrawn, and the ECA was ligated at the site of opening. The rats were then sutured and placed back into the cage, and allowed to reperfuse for 24 h. Room temperature throughout the operation was kept at 24-25° C. The rats were placed on the heating plate of 37° C. to maintain the body temperature throughout the operation. The administration was performed 15 minutes after ischemia.

Grouping and Drug Administration
Rats were divided into eight groups with 10 rats in each group. Group 1 was vehicle control with 1 ml/kg of vegetable oil; groups 2) and 3) were 40 and 80 mg/kg of dl-NBP; groups 4) and 5) were 20 and 40 mg/kg of d-NBP; groups 6) and 7) were 20 and 40 mg/kg of l-NBP; and group 8 was 0.1 mg/kg of MK801. Animals in groups 1-7 were orally administered, and animals in group 8 were intraperitoneally administered.

Neurological Behavioral Evaluation

Neurological behavioral observation was conducted after 24 h of ischemia. Rats were lifted up by tail 1 inch away from the ground, and the conditions of both forelimbs were observed; both shoulders were pushed to observe if there was any difference between the resistances by both sides; the rats were placed down to the ground and their walking conditions were observed. Scores were given in accordance with the following criteria.

0: strong forelimbs, symmetrically stretching towards the ground; identical resistance of both shoulders, and normal walk.
1: contralateral shoulder flexion, forelimb flexion; identical resistance of both shoulders, and normal walk.
2: contralateral shoulder flexion, forelimb flexion; decreased resistance of contralateral shoulder to push; and normal walk.
3: contralateral shoulder flexion, forelimb flexion; decreased resistance of contralateral shoulder to push; and circling when walking
4: contralateral shoulder flexion, forelimb flexion; and unable to autonomously move. The higher the score is, the more severe the behavioral disorder of the animal is.

Measurement of Cerebral Infarct Volume 24 h after operation, the rat was anesthetized with 100 mg/kg of sodium pentobarbital and decapitated. The brain was then rapidly removed, cut into six coronal sections (each of the first to the fifth section was 2-mm-thick, and the sixth section was 4-mm-thick), then rapidly placed into 5 ml of the solution containing 1.5 ml of 14% TTC and 0.1 ml of 1M $K_2HPO_4$ lightproofly. After incubation at 37° C. for 30 minutes, during which overturning was conducted every 7-8 minutes. After staining with TTC, the normal brain tissue showed rose colour, while the infarct tissue showed white with defined boundary. After incubation, each group of brain sections were arranged in order, and taken photos with a digital camera for storage. Each section was analyzed with a computerized image analyzer system (SPOT 3.5 software), and the infarct volume was calculated by integrating infarct area. The infarct volume was expressed as percentage of cerebral hemisphere to avoid the influence of cerebral edema. The equation for calculation is: cerebral infarct volume (%)=(volume of un-operated hemisphere−volume of un-infarcted portion of operated hemisphere)/volume of un-operated hemisphere.

Statistical Analysis

The results were expressed as mean±standard error. Neurological behavioral score and cerebral infarct volume were statistically analyzed using one-way ANOVA and the difference between groups using posthoc LSD test. Result was considered to show a significant difference when $p<0.05$.

Results

Effects of Optical Butylphthalide on Cerebral Infarct Volume of tMCAO Rats

The presence of significant difference between different groups analyzed by one-way ANOVA indicates that infarct volume is very significantly and dose dependently reduced in l-NBP group (both 20 mg/kg and 40 mg/kg). The reduction effect in the group of 40 mg/kg l-NBP was the best, and the infarct volume was reduced by up to 80.4% ($p<0.001$, vs. vehicle group). The therapeutic effect in this group was similar to that of MK801 group (infarct volume was reduced by 81.8%, $p<0.001$), while no significant effect was observed in d-NBP and dl-NBP groups (see FIGS. 1 and 2). The results above show that the reduction effect of l-NBP on the infarct volume is better than that of d-NBP. Although the infarct volumes in dl-NBP (80 mg/kg) and d-NBP (40 mg/kg) groups were reduced as compared with vehicle control, there was no statistically difference between them, suggesting that the presence of d-NBP in dl-NBP possibly antagonises the effect of l-NBP.

Behavioral Evaluation

Figure 3:
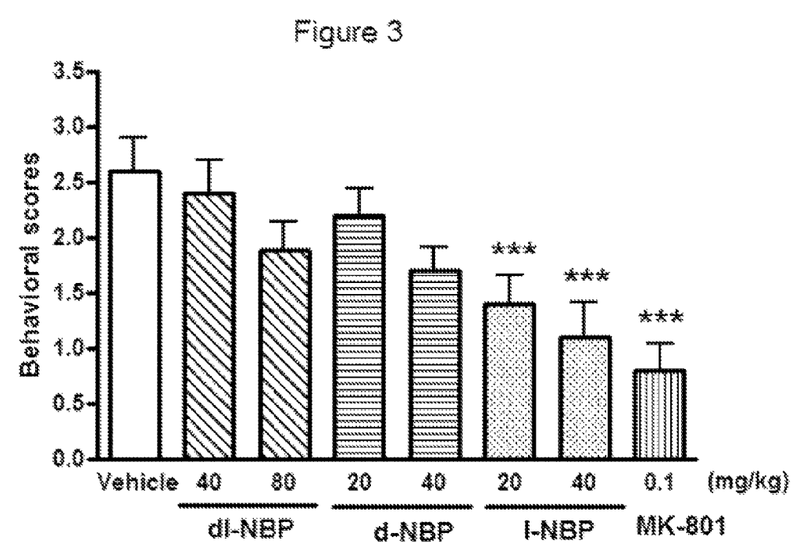
FIG. 3 shows the effects on the behavioral score of rats of administering NBP by gavage 15 minutes after transient middle cerebral artery occlusion. The data are expressed as mean±standard error.
*$P<0.05$, $P<0.01$, *$P<0.001$, vs. vehicle group.

The neurological score of most animals in vehicle control group were 2, manifested as contralateral forelimbs flexion and decreased resistance of contralateral extensor to lateral push. Contralateral circling occurred in fewer rats, and graded as 3. Even fewer animals only manifested as contralateral forelimb flexion and graded as 1; or had severe symptoms and unable to autonomously move, which was graded as 4. The mean of neurological score was 2.6±0.3. Oral administration of 20 and 40 mg/kg of l-NBP 15 minutes after ischemia was both shown to ameliorate the neurological symptoms (1.4, $p<0.01$, and 1.1, $p<0.001$), and the potency of MK801 was the most significant (0.8, $p<0.001$), while no significant improvement was observed in groups of d-NBP and dl-NBP. As for animals in MK801 treatment group, although the symptoms induced by cerebral ischemia was significantly reduced, the limbs were weak, and staggered when sprawling, ataxia occurred, and unilaterally circled. The behavioral evaluation suggested that the extent of behavioral improvement of drug is in parallel with the reduction effect of the drug on infarct volume (see FIG. 3).

Discussion

The models previously used by us are permanent focal ischemia (by burning brain middle artery), while transient focal cerebral ischemic model (2 hours of ischemia plus 24 hours of reperfusion) is used in this study. The latter has larger cerebral infarct volume than the former. Although the dose of dl-NBP selected is the same as that of previous, dl-NBP has no reduction effect on cerebral infarct volume at the doses being used (40 mg/kg and 80 mg/kg). This difference between the results is due to the difference between the two models.

The present invention was conducted on the levels of biochemistry, molecular biology and on animal level, and consistent results were obtained, that is, the cerebral protective effect of l-NBP is higher than that of d-NBP and dl-NBP, and the presence of d-NBP in dl-NBP antagonises the action of l-NBP, so that the protective effect against cerebral ischemia of dl-NBP is reduced.

As described in the literatures and according to the requirement of new drug discovery, in order to increase therapeutic effect and reduce toxic side effect, it is advisable to resolve the racemic drug into optical monomers, to make the characteristics of each clear, and to develop the optical isomer with potent effect or low toxic side effect into chiral new drug. As described in the context, l-NBP in racemic butylphthalide has relatively potent protective effect against cerebral ischemia. d-NBP not only has weaker effect, but also antagonises the protective effect of l-NBP against cerebral ischemia. Therefore, it is reasonable to develop L-butylphthalide into a new chiral drug for the treatment of acute ischemic cerebral stroke.

Previous studies have shown that the inhibitory effects of l-NBP against platelet aggregation and thrombosis were similar to those of Aspirin and Ticlipidine. In addition, l-NBP also has cerebral protective effect and micro-circulation improving effect (d-NBP has no such effect), which are not possessed by Aspirin and Ticlipidine. Therefore, l-NBP has so wide a therapeutic spectrum, that it can be used for the treatment of acute ischemic cerebral stroke, as well as secondary prevention of the cerebral stroke, prevention of cardiac infarct, and treatment of peripheral vascular diseases. It is expected to produce important social benefit and economic benefit, so that it is promising to develop l-NBP into a drug for the treatment of cerebral stroke. The therapeutic effect of levorotatory butylphthalide on focal cerebral ischemia has not been described in the references both here and abroad.

The invention claimed is:

1. A method of using L-butylphthalide of formula (I) for reducing the volume of cerebral infarct in a subject suffering from cerebral infarct, comprising orally administering a therapeutically effective dose of L-butylphthalide of formula (I), (I)

to the subject 15 minutes after ischemia to reduce the volume of the cerebral infarct.

2. The method of use according to claim 1, wherein said cerebral infarct is induced by focal cerebral ischemia.

3. The method of use according to claim 1, wherein the therapeutically effective dose of said L-butylphthalide is 0.1-100 mg/kg per day.

4. A method of using L-butylphthalide of formula (I) for improving neurological behavioral symptoms in a subject suffering from cerebral infarct, comprising orally administering a therapeutically effective dose of L-butylphthalide of formula (I), (I)

to the subject 15 minutes after ischemia to improve the neurological behavioral symptoms induced by the cerebral infarct.

* * * * *

UNITED STATES PATENT AND TRADEMARK OFFICE
CERTIFICATE OF CORRECTION

PATENT NO. : 8,598,225 B2
APPLICATION NO. : 12/908520
DATED : December 3, 2013
INVENTOR(S) : Y. Feng et al.

Page 1 of 1

It is certified that error appears in the above-identified patent and that said Letters Patent is hereby corrected as shown below:

On the title page item (73) should read:

Assignee: CSPS ZHONGQI PHARMACEUTICAL TECHNOLOGY (SHIJIAZHUANG) CO., LTD.,
SHIJIAZHUANG (CN)

INSTITUTE OF MATERIA MEDICA, CHINESE ACADEMY OF MEDICAL SCIENCES,
BEIJING (CN)

Signed and Sealed this
Seventh Day of April, 2015

Michelle K. Lee
*Director of the United States Patent and Trademark Office*